United States Patent [19]

Smith et al.

[11] Patent Number: 4,532,120
[45] Date of Patent: Jul. 30, 1985

[54] SILANE PURIFICATION PROCESS

[75] Inventors: Isaac L. Smith; Gunner E. Nelson, both of Baton Rouge, La.

[73] Assignee: Ethyl Corporation, Richmond, Va.

[21] Appl. No.: 566,279

[22] Filed: Dec. 28, 1983

[51] Int. Cl.$^3$ .............................................. C01B 33/04
[52] U.S. Cl. .................................... 423/347; 423/210; 423/299; 436/103; 436/182
[58] Field of Search .......... 55/73; 423/210 R, 210 M, 423/210 S, 299, 347; 436/103, 182

[56] References Cited

U.S. PATENT DOCUMENTS

| | | | |
|---|---|---|---|
| 2,971,607 | 2/1961 | Caswell | 55/73 |
| 2,987,139 | 6/1961 | Bush | 55/73 |
| 3,041,141 | 6/1962 | Shoemaker et al. | 423/347 |
| 3,043,664 | 7/1962 | Mason et al. | 423/347 |
| 3,446,605 | 5/1969 | Finholt | 423/299 |
| 3,512,932 | 5/1970 | Stern et al. | 423/299 |

OTHER PUBLICATIONS

Preparation of High-Purity Silicon from Silane, Charles H. Lewis et al.
1961, J. Electrochemical Society, Lewis et al.

Primary Examiner—Edward J. Meros
Assistant Examiner—Robert Alway
Attorney, Agent, or Firm—Donald L. Johnson; John F. Sieberth; John F. Hunt

[57] ABSTRACT

A process for the removal of and analysis of phosphine and arsine impurities in silane gas. Silane gas which normally contains the impurities of $AsH_3$ and $PH_3$ is contacted with a solution of $NaAlH_4$ in dimethoxyethane, other ether or amine to remove the impurities therefrom. The dimethoxyethane or other ether solution may then be hydrolyzed with water or alcohol to evolve hydrogen gas from the $NaAlH_4$ and to re-evolve phosphine and arsine which may then be quantitatively determined by gas chromatography, atomic absorption, or other means.

38 Claims, No Drawings

4,532,120

SILANE PURIFICATION PROCESS

BACKGROUND OF THE INVENTION

1. Field of the Invention

This invention relates in general to purification of gases and in particular to an advantageous method for the removal of phosphine and arsine from silane as well as the quantitative analysis of phosphine and arsine in silane.

2. Description of the Prior Art

Silane gas is pyrophoric and those skilled in the art recognize that it reacts with many substances. The semiconductor industry uses large amounts of silicon which are produced from gases including silane. Sinoe phosphine ($PH_3$) and arsine ($AsH_3$) are common contaminants in silane and are also known to affect the electrical properties of semiconductor silicon, gases used for the prep ration of such silicon must necessarily be low in content of these impurities to reduce contamination of the silicon product.

Thus there exists a need for a process to remove arsine and phosphine from silicon while guarding against reaction of the silane gas containing the impurities.

The semiconductor industry often requires a silicon starting material having as little as a few parts per billion or a few tenths of one part per billion of phosphorus or arsenic. This often may only be achieved by starting with a silane gas precursor which contains equally small quantities of contaminants. Since such tiny portions of contaminants are critical, it has been extremely difficult to devise such precise analytical techniques as will determine the amount of phosphine and arsine in a sample of silane gas.

SUMMARY OF THE INVENTION

The present invention is directed to the problem of removing arsine and phosphine impurities from silane gas while avoiding reaction with or contamination of the silane gas itself during purification.

The present invention offers the advantage of being able to determine very minute traces of arsine and phosphine impurities in a sample of silane gas. The advantage of the present invention is obtained by concentrating the trace impurities from a large volume of silane gas and then analyzing the concentrated portion in equipment with relatively high lower detection limits so as to calculate the contamination of the original silane sample.

Thus, the present invention is a process for the removal of phosphine or arsine from silane, said process comprising intimately contacting silane gas containing phosphine or arsine with a liquid mixture consisting essentially of an innocuous reaction medium and an alkali metal aluminum tetrahydride and recovering the purified silane gas.

The present invention is also a process for the analysis of phosphorus or arsenic content in silane, said process comprising intimately contacting silane gas containing phosphine or arsine with a liquid mixture containing alkali metal aluminum tetrahydride and then determining the amount of phosphorus or arsenic in the liquid mixture.

The present invention is also an analytical method for measuring the phosphine and arsine content of a silane sample, said process comprising the steps of intimately contacting the sample with a solution of alkali metal aluminum tetrahydride to react the phosphine and arsine therewith so as to remove at least about 90% of the phosphine and arsine from the silane: hydrolyzing the solution to evolve hydrogen gas from the alkali metal aluminum tetrahydride and re-evolve phosphine and/or arsine gases in a closed space, and determining the amount of arsine and phosphine concentrated in the hydrogen gas.

DESCRIPTION OF THE PREFERRED EMBODIMENTS

Various alkali metal aluminum tetrahydrides may be used according to the process of the invention. These compounds include sodium aluminum tetrahydride, lithium aluminum tetrahydride, and potassium aluminum tetrahydride. Sodium aluminum tetrahydride is most preferred.

The alkali metal aluminum tetrahydrides of the present invention are used in a liguid mixture so that the silane gas may be contacted with the mixture, preferably, the liquid mixture is a solution containing the alkali metal aluminum tetrahydride. More preferably, the solvents used for dissolving the alkali metal aluminum tetrahydrides are ethers. Ethers usable according to the present invention include tetrahydrofuran (THF), dimethoxyethane (monoglyme), and the dimethylether of diethylene glycol (diglyme). Various other ethers may also be used according to the invention. For purification, monoglyme is preferred because of its stability and good solubility of the various alkali metal aluminum tetrahydrides including sodium aluminum tetrahydride. For silane analysis, a less volatile compound, such as diglyme is preferred.

Tertiary amines may also be used as a solvent according to the invention. Suitable tertiary amines include the trialkylamines such as triethylamine, tri-n-propylamine, tributylamine as well as mixed alkyl amines.

Various hydrocarbon mediums may also be used according to the invention but usually form liquid mixtures which are not solutions of the alkali metal aluminum tetrahydride.

Since solid-gas reactions are known to proceed relatively slowly, a solution of the alkali metal aluminum tetrahydride is preferred over a liquid mixture since the liquid mixture approximates the contact between a solid alkali metal aluminum tetrahydride and a gas, silane. Thus, liquid mixtures of the alkali metal aluminum tetrahydride which are not solutions are expected to react relatively slowly with the impurities of the silane gas.

Most notably, the invention is advantageous in that the silane gas to be purified and/or analyzed, a commodity which is difficult and expensive to obtain, passes through the procedure and method of the present invention without detrimental effect to the silane itself.

We have found that silane gas, even when evolved from alkali metal aluminum tetrahydride solutions during silane production is of insufficient purity for the manufacture of silicon having an end use in semiconductors or photovoltaics. We have also learned that storage of silane in containers results in contamination with phosphine and arsine. Thus, the present invention is directed to a process for purifying as-produced silane or otherwise contaminated silane in preparation for its reduction to high purity silicon.

We have found that intimately contacting a liquid mixture of alkali metal aluminum tetrahydride with contaminated silane is effective for the removal of $AsH_3$ and $PH_3$, without reacting with the silane gas containing these impurities. Furthermore, we have also devised a method for quantitatively determining the amount of arsine and phosphine in a silane gas sample.

By intimately contacting we mean such contact between the alkali metal aluminum tetrahydride liquid mixture and the gaseous silane as will enhance the factors of bubble submersion time, bubble size, mass transport to bubble-liquid interface, and the like. Intimate contacting may be carried out by high shear agitation means including rapid stirring. Stirring is preferably carried out at a rate equivalent to at least 200 RPM's in laboratory glassware equipment. More preferably, stirring is conducted in heavier equipment at as high as 1000 RPM's or higher where possible.

Superatmospheric pressure also tends to improve the efficiency of the inventive method. Pressures of only two atmospheres increase the rate of $PH_3/AsH_3$ removal during contact of silane and the tetrahydride liquid mixture. Even higher pressures should further enhance the removal and are preferred.

Of course both agitation and pressure have upper limits of practical operation and diminishing returns at the maximum $PH_3/AsH_3$ removal rate from silane depending upon the particular equipment alkali metal aluminum tetrahydride, and liquid used.

A very effective method of intimate contact is bubbling silane through a tall column of the liquid mixture or more preferably directing a stream of silane through a countercurrent flow of the liquid mixture as in a column or conventional scrubber. This may be arranged to receive silane gas as it is produced, from a reactor.

The purification process of the invention is carried out in a liquid mixture consisting essentially of an innocuous reaction medium and an alkali metal aluminum tetrahydride. By this we mean that the liquid mixture, while it may contain some small portions of impurities or the like, does not contain a significant portion of silane-producing reactant such as is present during the manufacture of silane from an alkali metal aluminum tetrahydride and a silicon tetrahalide (e.g., $SiCl_4$ and $LiAlH_4$). Rather, the purification process of the invention is carried out in an environment that enhances conta ct of "contaminated" silane with a purifying liquid mixture that is primarily an innocuous reaction medium, preferably a solvent, and alkali metal aluminum tetrahydride.

For silane purification, preferably, the liquid mixtures and solutions of the invention are usually sufficiently free of other contaminants and sources of phosphorus or arsenic. For analysis the alkali metal aluminum tetrahydride is preferably purified by known means prior to use in order to reduce the analytical blank.

We have found that an agitated solution of sodium aluminum tetrahydride, for example, is usually effective to remove about 90% of the phosphine and greater than 90% of the arsine present in a silane gas. These approximate numbers of 90% and greater than 90% seem to hold true whether the contamination of phosphine and arsine in the silane gas is of relatively large amount like 100 parts per million or even if it is of a relatively minuscule amount of about one part per billion.

The silane solution to be purified or analyzed according to the present invention may be contacted with a liquid mixture of alkali metal aluminum tetrahydride according to the invention by various means. One means would be a countercurrent flow of silane gas through a liquid mixture of, for example, sodium aluminum tetrahydride in monoglyme. Various columnar and bedlike devices may be used for contacting the silane gas with the liquid mixture according to the invention.

The important aspect of the analytical method of the present invention is that minute portions of phosphine and arsine present in a silane stream may be gathered into a liquid mixture by an alkali metal aluminum tetrahydride and then re-evolved as phosphine or arsine or the like as a gas in a concentrated form thereby making quantitative analysis more practical. This makes available for determination of these trace impurities the various quantitative analysis techniques normally used where only large amounts of material are found. For example, about 2,000 liters of a silane gas contaminated with trace impurities of phosphine and arsine at about the 0.1 parts per billion level may be contacted with a relatively small solution of sodium aluminum tetrahydride in order to gather about 90% of the contaminant phosphine and arsine into the relatively small volume of hydride in ether. Although the level of contamination is small by normal analytical standards (although large by high purity silicon standards), the concentration of phosphine and arsine may be brought above minimum detection limits for the equipment in question. This then enables an analyst to use a photoionization detector with a 10 PPb thresh-hold or a molybdenum blue orthophosphate test.

According to the analytical method of the invention the phosphine and arsine which have been reacted and gathered into the solution or liquid mixture of the invention may be quantitatively determined by various means. Preferably, the phosphorus and arsenic content in the liquid are first separated before the quantity is determined. More preferably, the phosphorus or arsenic values are liberated as $PH_3$ or $AsH_3$. Still more preferably, the $PH_3$ and $AsH_3$ are evolved into a closed space, such as the headspace above the liquid. An expandable container is suitable for this purpose. Most preferably the $AsH_3$ and $PH_3$ are re-evolved by hydrolysis. Various agents may be used to re-evolve phosphine and arsine. Among these are water and methanol. A small portion of water or other hydrolysis agent may be injected into the liquid mixture containing alkali metal aluminum tetrahydride in such a manner as to re-evolve substantially all of the phosphine or arsine in the liquid mixture. The hydrolysis may be carried out in a closed expandable bag such that the phosphine and arsine are re-evolved with hydrogen gas from hydrolysis of the alkali metal aluminum tetrahydride into the head space above the liquid mixture. Thereafter the gas may be readily analyzed by such techniques as gas chromatography (using a photoionization detector) or by atomic absorption or other direct analysis techniques which have lower limits of detection not usually suitable for trace impurities in silane.

Other suitable agents to hydrolyze the tetrahydride and the phosphorus/arsenic values are any compounds with a source of active hydrogen. These include acids such as propionic, nitric, sulfuric, acetic, and HCl; primary and secondary amines such as n-propylamine, n-butylamine diethylamine, mixed dialkylamines and others; alcohols such as methanol, ethanol, isopropanol, tertbutanol, and sec-butanol as well as phenols and alkylated phenols. Where the liquid mixture is a monoglyme or similar solution of alkali metal aluminum tetrahydride, it is preferred to pump in a ten percent solution of water in diglyme from a syringe or the like.

Alternatively, the hydrogen gas containing phosphine and arsine in the head space above the liquid or liquid-solid mixture remaining after hydrolysis of the alkali metal aluminum tetrahydride may be used in other analytical techniques. For example, the phosphine gas may be swept to an oxidizing solution such as a hypochlorite. Preferably a sodium hypochlorite solution and then acidified and boiled to form orthophosphate ($PO_4^{-3}$). In this manner, the phosphorus content may then be determined by colorimetric phosphate solution procedures known to those skilled in the analytical arts. Such a procedure is commonly referred to as a standard orthophosphate procedure or molybdenum blue orthophosphate procedure. Notably, the sodium hypochlorite solution may not be used directly because silane reacts explosively therewith.

The amount of removal of phosphine and arsine gas along with the hydrogen gas evolved upon hydrolysis is dependent upon the technique used for contacting water or other hydrolysis agent with the alkali metal aluminum tetrahydride liquid mixture. A gas washing bottle with a side septum for injection of hydrolysis agent may be used in a manner where the gas liquid contact is high so as to evolve all of the contained phosphorus and arsenic values as $PH_3/AsH_3$.

The major advantage of the present invention is that it is now possible to concentrate the relatively minute quantities of phosphine and arsine present in a silane gas into a much smaller volume wherein the impurities may be analyzed with increased sensitivity. A better understanding of the invention will be had by a review of the examples of the invention as given below.

We observed that the removal of phosphine from the silane or mixed gas solutions is more effective with high rates of agitation as shown in the tables below. Various methods of agitation may be used within the scope of the invention so long as the phosphine and arsine are reacted to be taken up in the scrubber solution and then optionally re-evolved for testing to determine purity of the silane stream so treated or to determine the purity of the incoming silane stream. According to the invention one may test a large volume of a silane stream to determine the amount of phosphine or arsine contamination to determine whether additional purification is required or whether the silane stream may then be used to form silicon in a high purity silicon manufacturing process wherein the silicon is ultimately used for semiconductor or photovoltaic applications. One of the most advantageous features of the present invention is that the liquid mixtures for scrubbing a silane gas flow according to the present invention do not react with silane and thus do not affect the ultimate use of the silane usually in the production of semiconductor or photovoltaic grade silicon.

In a large scale purification operation we estimate that about a 15% solution of sodium aluminum tetrahydride in monoglyme is the best form of purification according to the process of the present invention as now known to us.

In the Examples below, a gas flow containing $AsH_3$ and $PH_3$ was first sampled and analyzed. The levels of $AsH_3$ and $PH_3$ were set high enough for conventional detection. The gas flow was then passed through a liquid mixture and again immediately sampled and analyzed. The Examples were carried out to show the removal of $PH_3$ or $AsH_3$ from silane. During the course of the experiments we found that the rates of removal of $PH_3$ and $AsH_3$ from nitrogen/silane mixtures and nitrogen gas alone are about the same as for silane alone. Of course, silane gas in practice requires handling and use of reagents that will not react therewith as compared to inert nitrogen.

EXAMPLE I

A 150 milliliter scrubber solution of $NaAlH_4$ in monoglyme was charged to a 250 milliliter round bottom flask. The flask was equipped with a septum cover on an opening near the top, a magnetic stirring bar operated at about 200 rpm. and a second opening near the top fitted with a dip leg in the stop cock for entry of the silane flow so as to be dispensed near the bottom of the liquid level in the round bottom flask in the area of high agitation. The dip leg tube was fitted with a coarse porosity dispersion frit. The neck of the round bottom flask contained a cooling water tube for the flow of cooling water in and out of the neck area to cool the effluent silane. The neck of the flask was fitted with a two-way valve apparatus so that the effluent silane bubbled through the 150 milliliter scrubber solution could be sent to a burner as desired or to a 250 milliliter mass spectroscopy sample bottle. The entire flask and apparatus was kept in a water bath on a stirring hot plate. A small magnetic stirring bar was operated at 200 RPM's. Phosphine and arsine samples were available in nitrogen gas. The supply of phosphine gas contained about 1011 ppm $PH_3$ in nitrogen. The supply of arsine gas contained about 8 ppm $AsH_3$ in nitrogen. The nitrogen gas supply was essentially free of contaminants and the supply of silane was known to contain fewer than 10 parts per billion phosphine and arsine. A flow of gases was started with about 1.1 standard cubic feet per hour of the arsine source gas, 0.4 standard cubic feet per hour of the phosphine source gas, 1.5 standard cubic feet per hour of the nitrogen gas, and about 1.5 standard cubic feet per hour of the silane gas. After the equipment had been purged with nitrogen gas alone, the flow of gases as described above was directed to a 250 milliliter mass spectroscopy sample bottle. When the bottle was filled, the sample was immediately analyzed with a photoionization detector and the number of integrater counts for the sample was noted. While the first sample was being analyzed, the flow of gases were directed through the sparging tube and through the coarse porosity dispersion frit into the stirred solution in the round bottom flask. The silane gas was evolved and collected in a second 250 milliliter mass spectroscopy sample bottle and again immediately tested. The number of integrater counts in the sample which had passed through the stirred solution of sodium aluminum tetrahydride in monoglyme was recorded and this value in conjunction with the value from the first sample was used to calculate the percent removal of phosphine and arsine from the gas flow. The samples from each of the bottles were first run through gas chromatography equipment so as to identify the phosphine and arsine which elute separately. Notably, the arsine removal could only be calculated as a "greater than" percent figure since a small portion of some other compound was eluting at about the same place on the G.C. For ease of calculation, the entire area of the peak for arsine in the second sample was used as entirely arsine. Thus, this was the most arsine which could remain in the second sample.

Subsequent testing of samples which had set out for even short periods of time evidenced the instability of the phosphine and arsine samples by a rapid decrease in the total integrater counts obtained on such subsequent sample injections from the filled containers. This is a wall effect with the containers since a sample tends to reach an equilibrium concentration of such impurities in certain containers.

For this example and for Example II, the percent removal of phosphine or arsine were easily calculated by atomic absorption and gas chromatorgaphy with a photoionization detector, according to the following formula.

$$\% \text{ Removal} = 100 \times \frac{\text{Int. Counts, Sample 1} - \text{Int. Counts, Sample 2}}{\text{Int. Counts, Sample 1}}$$

The results fo the above experiments using various solutions at various operating temperatures are given in Table I below.

TABLE I

Tests Conducted in Glass Reactor

| Scrubber Test Solution | Temp., °C. | Percent Removal For | |
|---|---|---|---|
| | | $PH_3$ | $AsH_3$ |
| 0.53%[2] $NaAlH_4$ in THF | 24 | 90 | >98 |
| | 44 | 88 | >90[2] |
| | 66 (Reflux) | 86 | >90[2] |
| 10.4% $NaAlH_4$ in THF | 24 | 58 | >99 |
| | 50 | 44 | >90[2] |
| THF alone | 24 | None | 50 |
| 10.6% $NaAlH_4$ in Dimethoxyethane | 24 | 60 | >95[2] |
| | 50 | 60 | >95[2] |
| | 75 | 65 | >95[2] |
| 8.1% $NaAlH_4$ in Diglyme | 22 | 34 | >90[2] |
| | 50 | 37 | >90[2] |
| | 75 | 48 | >90[2] |

[1] All $NaAlH_4$ values given are calculated from gas evolution analyses.
[2] Since other components of small quantity were eluting at about the same peak as arsine, only a "greater than" percent removal can be given.

EXAMPLE II

The same general procedure was followed as in Example I except that since we had learned that the removal of phosphine and arsine is about the same according to this invention from silane as it is from nitrogen or mixtures of nitrogen and silane, some of the experiments in Example II were run using nitrogen only to demonstrate the workability of the invention. The same sources of arsine and phosphine in nitrogen solutions were supplied to a flow of either nitrogen or silane/nitrogen mixture as for Example I. In this Example, however, the gas flow was provided to a one liter baffled autoclave with a three bladed propeller stirrer. The autoclave was fitted with a dip tube feed of the gas supply below the agitator. The high pressure autoclave was used not for carrying out a high pressure reaction but for the purpose of conducting the invention at high agitation without leakage. The effluent from the autoclave reactor passed through a condenser and into a valve like that used in Example I so that the flow could be switched from a route to a burner for the silane to a route to be collected in a 500 milliliter sample bomb for the hydrogen, phosphine, and arsine mixture. In both this example and Example I, samples of the gas flow to the reactors were collected in a separate bomb for comparison. This enabled us to calculate the percent removal based upon standard analytical equipment. A sample 1 of the gas flow was first taken. After the gas flow had continued through a 526 gram sample of dimethoxyethane containing 8% by weight sodium aluminum tetrahydride, sample 2 was taken. Again the percent removal was calculated by the formula given in Example I and the results are tabulated in Table II below.

Tests Conducted in 1 Liter Autoclave

TABLE II

| RPM | Temp. °C. | Pressure psig | Carrier gas | % Removal For | |
|---|---|---|---|---|---|
| | | | | $PH_3$ | $AsH_3$ |
| 450 | 22 | 0 | $N_2$ | 91 | 90 |
| 1000 | 26 | 0 | $N_2$ | 62 | 1 |
| 1400 | 22 | 0 | $N_2$ | 98 | >99 |
| 1400 | 21 | 20 | $N_2$ | 99 | >99 |
| 1400 | 47 | 0 | $N_2$ | 96 | >99 |
| 1400 | 26 | 0 | $N_2$ | 94 | 1 |
| 450 | 20 | 0 | $N_2/SiH_4$ | 68 | 1 |
| 1000 | 23 | 0 | $N_2/SiH_4$ | 94 | 1 |
| 1400 | 24 | 0 | $N_2/SiH_4$ | 95 | 1 |

[1] Source of $AsH_3$ exhausted - none used.

We noted that a slight pressure increased the removal of phosphine from a nitrogen solution and as a general rule we found that increased pressure increased the percent removal of phosphine from a gas. We found that arsine is generally much more easily and completely removed than phosphine and we generally directed our efforts to removal of phosphine at a high level which always resulted in the very efficient removal of arsine as well.

We also noticed that the use of the invention was effective for removal of a portion of the sulphur compounds including $SO_2$ which were found in some samples of silane gas. Similarly, we found that fluoride compounds are fairly well removed by use of the invention. Also diborane is removed. In particular, the contaminant sodium aluminum tetrafluoride present when the silane is produced from silicon tetrafluoride and sodium aluminum tetrahydride or the like, is fairly readily removed by using a countercurrent flow of reactant alkali metal aluminum tetrahydride in ether to the effluent silane from a silane reactor. Separate downstream scrubbers are also effective.

In other experiments, phosphorus at the level of 100 parts per million was reduced to less than 20 parts pe billion in a nitrogen stream and in a silane stream by passing each stream through an agitated solution of two percent purified $NaAlH_4$ in diglyme at 90° C. The lower limit of $PH_3$ detection is 20 ppb for the vapor phase chromatography equipment used. These experiments indicate that higher temperatures may enhance $PH_3$ removal.

In still another experiment, about 1 ml. of solution from the autoclave, after 15 minutes of contaminated gas flow (the glassware flow was operated for about ten minutes), was added to 149 mls. of a control solution of purified monoglyme containing $1.1 \times 10^{-6}$ grams phosphorus and two percent purified $NaAlH_4$. The phosphine and arsine gases were re-evolved from the solution along with $H_2$ by slowly injecting (pumping from a syringe) a solution of about 6 mls. distilled $H_2O$ in 44 mls. pure diglyme. The evolved (and re-evolved) gases were swept to a pure solution of sodium hypochlorite and colorimetric analysis revealed about $25 \times 10^{-6}$ grams phosphorus—an increase of about 24 micrograms from one liter of the purifying solution.

It can readily be seen that internal standards can be established and the volume of silane analyzed or purified along with the amount of liquid mixture can be recorded to analyze an unknown contaminated silane or to purify a silane of known contamination level.

The above description is the best mode of the invention now known to us. Additional experiments with other hydrolyzing agents such as methanol and other alcohols confirm that these agents may also be used according to the invention to hydrolyze the alkali metal aluminum tetrahydride and re-evolve the phosphine and arsine gases from the scrubber solution.

Of course it is possible to vary the method, apparatus, and other features of the invention without departing from the lawful scope or true spirit thereof. For example, one could use an apparatus similar to those described in Examples I and II for a purification process of a silane stream or a stream of gas comprising silane and another gas.

We claim:

1. A process for the removal of phosphine or arsine from previously synthesized silane, said process comprising intimately contacting silane gas containing phosphine or arsine with a liquid mixture consisting essentially of an innocuous reaction medium and an alkali metal aluminum tetrahydride and recovering the purified silane gas.

2. The process of claim 1 wherein said innocuous reaction medium is a solvent for the alkali metal aluminum tetrahydride.

3. The process of claim 2 wherein said solvent is a tertiary amine.

4. The process of claim 2 wherein said solvent is an ether.

5. The process of claim 4 wherein said ether is selected from the group consisting of tetrahydrofuran, diglyme, and monoglyme.

6. The process of claim 4 wherein said ether is monoglyme.

7. The process of claim 3 wherein said tertiary amine is triethylamine.

8. The process of claim 1 wherein intimately contacting comprises high shear agitation.

9. The process of claim 8 wherein high shear agitation comprises rapid stirring, at least about 200 RPM, so as to enhance the factors of bubble submersion time, bubble size, and mass transport to bubble-liquid interphase.

10. The process of claim 1 wherein intimately contacting comprises countercurrent flow of the silane with the liquid mixture.

11. The process of claim 2 wherein a solution of alkali metal aluminum tetrahydride is flowed countercurrent to a silane gas containing arsine and phosphine.

12. The process of claim 1 wherein said alkali metal aluminum tetrahydride is sodium aluminum tetrahydride.

13. The process of claim 12 wherein said liquid mixture is an ether solution.

14. The process of claim 13 wherein said ether is dimethoxyethane (monoglyme).

15. The process of claim 1 carried out at superatmospheric pressure.

16. The process of claim 1 carried out at a pressure of at least about two atmospheres.

17. A process for the analysis of phosphorus or arsenic content in previously synthesized silane, said process comprising intimately contacting silane gas containing phosphine or arsine with a liquid mixture containing alkali metal aluminum tetrahydride and then determining the amount of phosphorus or arsenic in the liquid mixture.

18. The process of claim 17 wherein said alkali metal aluminum tetrahydride is sodium aluminum tetrahydride.

19. The process of claim 17 wherein said liquid mixture is an ether solution.

20. The process of claim 17 wherein said liquid mixture is an ether solution containing alkali metal aluminum tetrahydride and said ether is selected from the group consisting of tetrahydrofuran, dimethoxyethane, and the dimethylether of diethylene glycol.

21. The process of claim 20 wherein said ether is the dimethylether of dielthylene glycol.

22. The process of claim 21 wherein said alkali metal aluminum tetrahydride is sodium aluminum tetrahydride.

23. The process of claim 19 wherein said determining the amount of phosphorus or arsenic in the liquid mixture after contacting the silane gas with the ether solution comprises hydrolyzing said solution to re-evolve phosphine or arsine along with hydrogen from the alkali metal aluminum tetrahydride.

24. The process of claim 23 wherein the re-evolved phosphine or arsine are analyzed by chromatography, atomic absorption, or colorimetric procedures.

25. The process of claim 23 wherein the re-evolved phosphine is reacted with a hypochlorite to form an orthophosphate for colorimetric analysis.

26. The process of claim 24 wherein said hydrolyzing is caused by the addition of water or alcohol.

27. The process of claim 17 wherein said intimately contacting comprises high shear agitation.

28. The process of claim 27 wherein said high shear agitation comprises rapid stirring, at least about 200 RPM, so as to enhance the factors of bubble submersion time, bubble size, and mass transport to bubble-liquid interphase.

29. The process of claim 17 wherein said intimately contacting comprises countercurrent flow of the silane with the liquid mixture.

30. An analytical method for measuring the phosphine and arsine content of a silane sample, said process comprising the steps of intimately contacting the sample with a solution of alkali metal aluminum tetrahydride to react the phosphine and arsine therewith so as to remove at least about 90% of the phosphine and arsine from the silane; hydrolyzing the solution to evolve hydrogen gas from the alkali metal aluminum tetrahydride and re-evolve phosphine and arsine gases in a closed space; and determining the amount of arsine and phosphine concentrated in the hydrogen gas.

31. The method of claim 30 wherein said alkali metal aluminum tetrahydride is sodium aluminum tetrahydride.

32. The method of claim 30 wherein said solution comprises an ether solution or a tertiary amine solution.

33. The method of claim 30 wherein said solution comprises an ether solution.

34. The method of claim 33 wherein the ether of said ether solution is selected from the group consisting of tetrahydrofuran, dimethoxyethane (monoglyme) and the dimethylether of diethylene glycol (diglyme).

35. The method of claim 34 wherein said ether is dimethylether of diethylene glycol.

36. The process of claim 30 wherein the amount of arsine and phosphine concentrated in said hydrogen gas is determined by gas chromatography, atomic absorption, or colorimetric procedures.

37. The method of claim 30 wherein said solution is hydrolyzed by water, an alcohol, an acid, or a primary or secondary amine to evolve $PH_3$ or $AsH_3$.

38. The method of claim 30 wherein said solution is hydrolyzed by water.

* * * * *

UNITED STATES PATENT AND TRADEMARK OFFICE
CERTIFICATE OF CORRECTION

PATENT NO. : 4,532,120

DATED : JULY 30, 1985

INVENTOR(S) : ISAAC L. SMITH, ET AL.

It is certified that error appears in the above-identified patent and that said Letters Patent is hereby corrected as shown below:

Column 1, line 15, reads "sinoe" and should read -- since --.

Column 1, line 19, reads "prep ration" and should read -- preparation --.

Column 2, line 19, reads "liguid" and should read -- liquid --.

Column 3, line 44, reads "conta ct" and should read -- contact -.

Column 6, line 13, reads "liguid" and should read -- liquid --.

Column 7, line 7, reads "chromatorgaphy" and should read -- chromatography --.

Column 7, line 11, reads "Int." and should read -- (Int. --.

Column 7, line 15, reads "fo" and should read -- of --.

Column 7, line 23, reads "$0.53\%^2$" and should read -- $0.53\%^1$ --.

Column 7, line 54, reads "wlthout" and should read -- without --.

UNITED STATES PATENT AND TRADEMARK OFFICE
CERTIFICATE OF CORRECTION

PATENT NO. : 4,532,120

DATED : JULY 30, 1985

INVENTOR(S) : ISAAC L. SMITH, ET AL.

It is certified that error appears in the above-identified patent and that said Letters Patent is hereby corrected as shown below:

Column 8, line 42, reads "pe" and should read -- per --.

Column 10, line 6, reads "dimethoxyethane, and" and should read -- dimethoxyethane (monoglyme), and --.

Column 10, line 7, reads "glycol." and should read -- glycol (diglyme). --.

Signed and Sealed this

Twenty-ninth Day of October 1985

[SEAL]

Attest:

DONALD J. QUIGG

Attesting Officer

Commissioner of Patents and Trademarks—Designate